(12) United States Patent
Kessler

(10) Patent No.: US 9,480,498 B1
(45) Date of Patent: Nov. 1, 2016

(54) TISSUE CUTTER

(71) Applicant: Yoel Kessler, Efrat (IL)

(72) Inventor: Yoel Kessler, Efrat (IL)

( * ) Notice: Subject to any disclaimer, the term of this patent is extended or adjusted under 35 U.S.C. 154(b) by 0 days.

(21) Appl. No.: 14/791,992

(22) Filed: Jul. 6, 2015

(51) Int. Cl.
A61B 5/00 (2006.01)
A61B 17/34 (2006.01)
A61B 17/32 (2006.01)
A61M 25/06 (2006.01)
A61M 25/09 (2006.01)

(52) U.S. Cl.
CPC ........... *A61B 17/3403* (2013.01); *A61B 17/32* (2013.01); *A61B 17/3415* (2013.01); *A61B 17/3494* (2013.01); *A61M 25/065* (2013.01); *A61B 2017/320052* (2013.01); *A61B 2017/3409* (2013.01); *A61M 25/09* (2013.01)

(58) Field of Classification Search
CPC ............ A61B 5/1411; A61B 5/15117; A61B 5/1519
USPC .......................................................... 606/182
See application file for complete search history.

(56) References Cited

U.S. PATENT DOCUMENTS

| 5,133,730 A | 7/1992 | Biro et al. |
| 5,662,669 A * | 9/1997 | Abidin ............... A61B 17/3213 30/151 |
| 5,797,940 A | 8/1998 | Mawhirt et al. |
| 5,843,108 A | 12/1998 | Samuels |
| 5,851,215 A | 12/1998 | Mawhirt et al. |
| 5,941,892 A * | 8/1999 | Cohn ................. A61B 17/3213 30/151 |
| 6,221,089 B1 * | 4/2001 | Mawhirt ............. A61B 5/1411 606/181 |
| 6,716,228 B2 | 4/2004 | Tal |
| 6,949,109 B2 * | 9/2005 | Iske .................... A61B 17/3211 30/162 |
| 7,341,596 B2 * | 3/2008 | Heppler ........... A61B 17/32093 606/167 |
| 8,167,897 B2 * | 5/2012 | Muto ................. A61B 17/3211 606/167 |
| 8,512,363 B2 * | 8/2013 | Heppler ............. A61B 17/3211 606/167 |
| 8,961,541 B2 | 2/2015 | Houser |
| 2004/0181246 A1 * | 9/2004 | Heppler ........... A61B 17/32093 606/167 |
| 2005/0177183 A1 * | 8/2005 | Thorne ................. A61B 17/32 606/167 |
| 2010/0010529 A1 | 1/2010 | Shi |

\* cited by examiner

*Primary Examiner* — Julie A Szpira
(74) *Attorney, Agent, or Firm* — Sughrue Mion, PLLC

(57) ABSTRACT

A tissue cutter includes a housing, a blade, a pivot, and a blade spring. The housing is shaped so as to define a channel that has proximal and distal openings and a central longitudinal axis, and is shaped for slidable disposition therein of a hollow tubular element having a tapered distal portion. The blade which extends alongside the central longitudinal axis, and defines a sharp cutting surface that reaches a distal-most point of the blade and faces away from the central longitudinal axis. The pivot couples the blade to the housing such that the blade is rotatable with respect to the housing around a pivot point of the blade. The blade spring is arranged to apply a force to the blade that pushes a distal portion of the blade against the tapered distal portion of the hollow tubular element when the blade is positioned alongside the tapered distal portion.

30 Claims, 11 Drawing Sheets

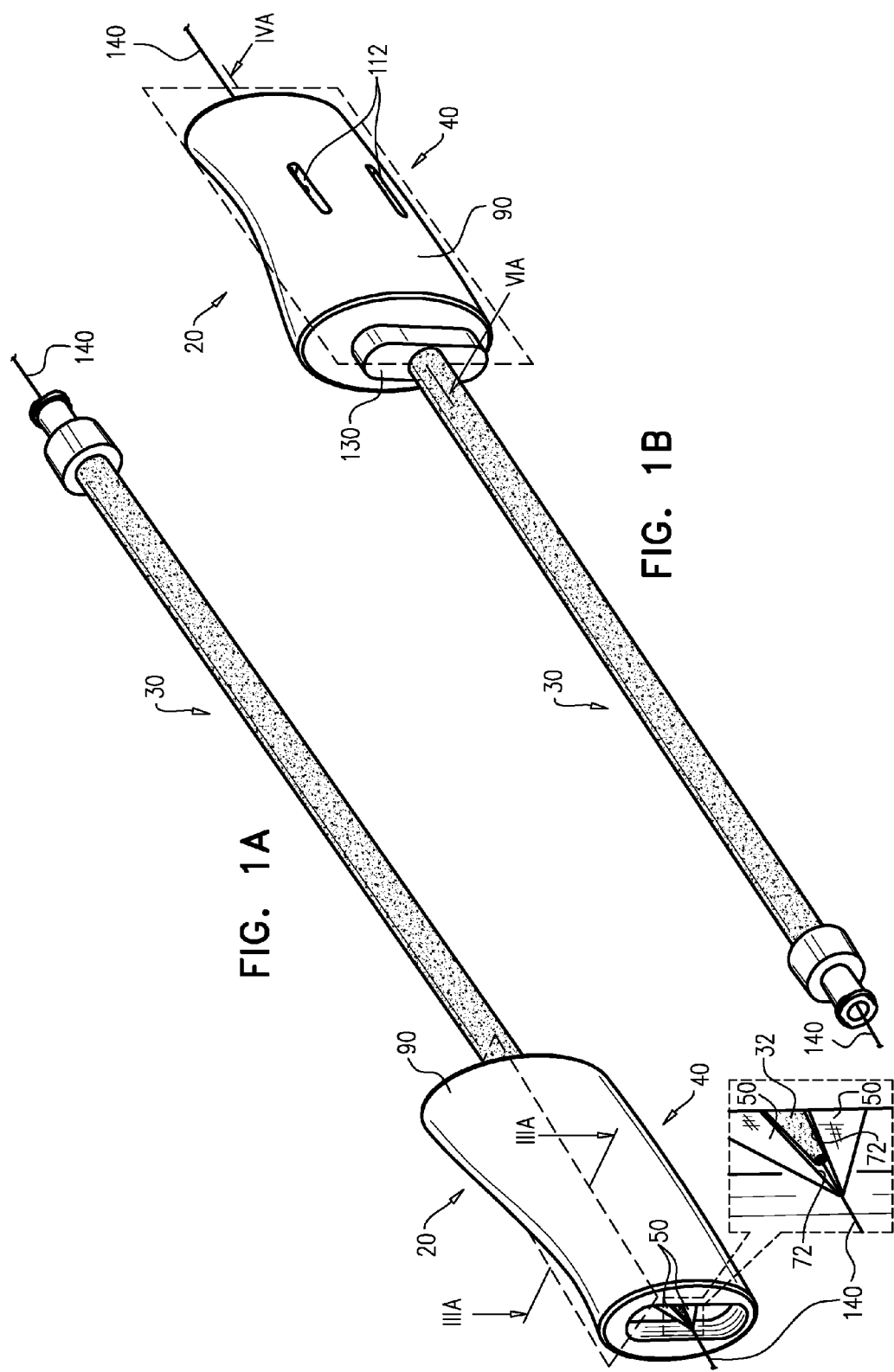

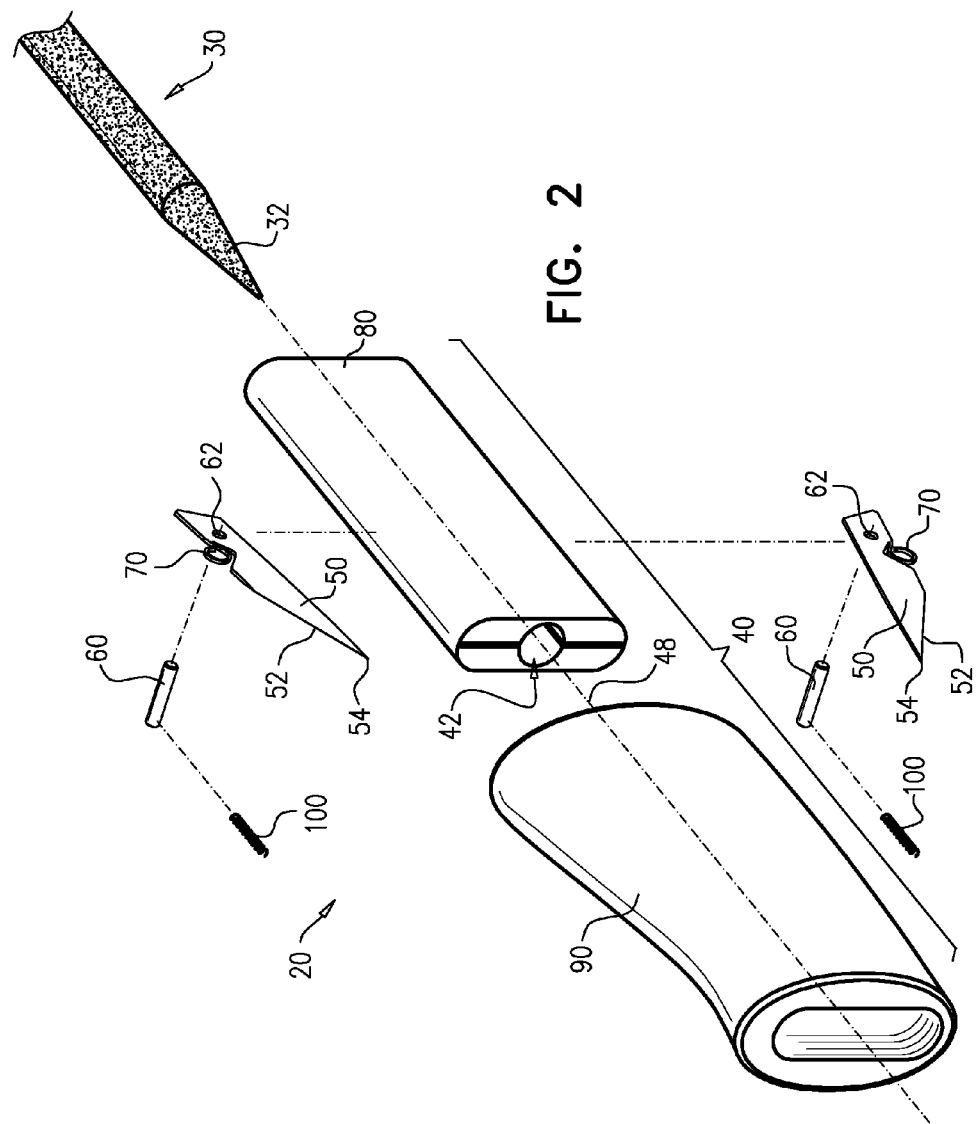

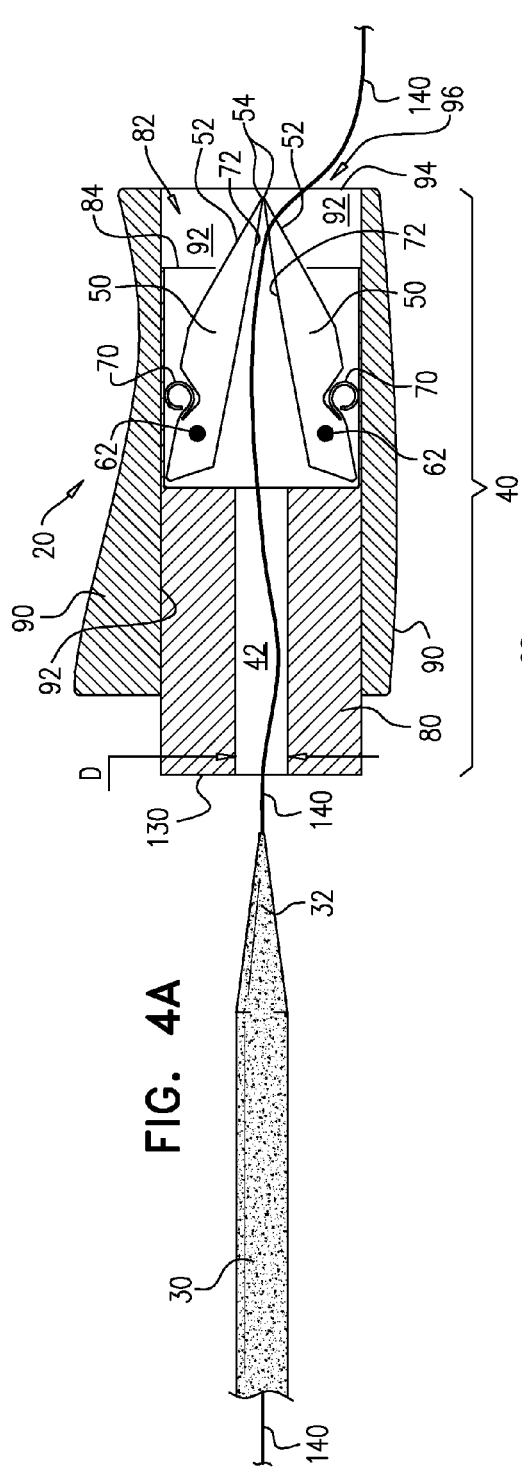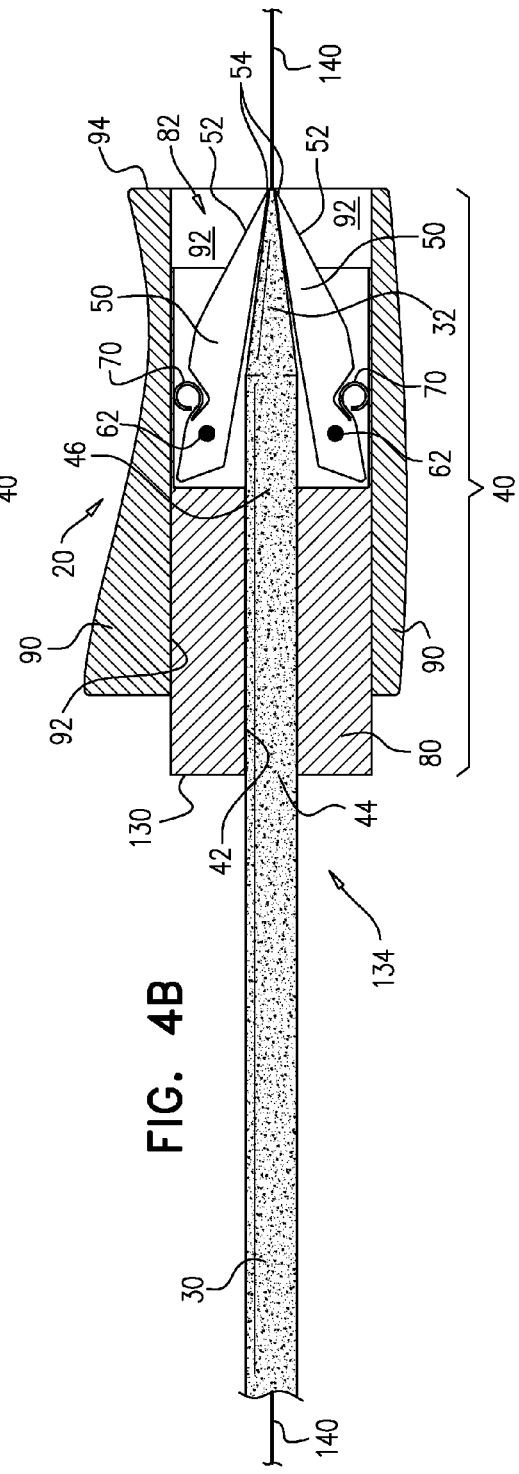

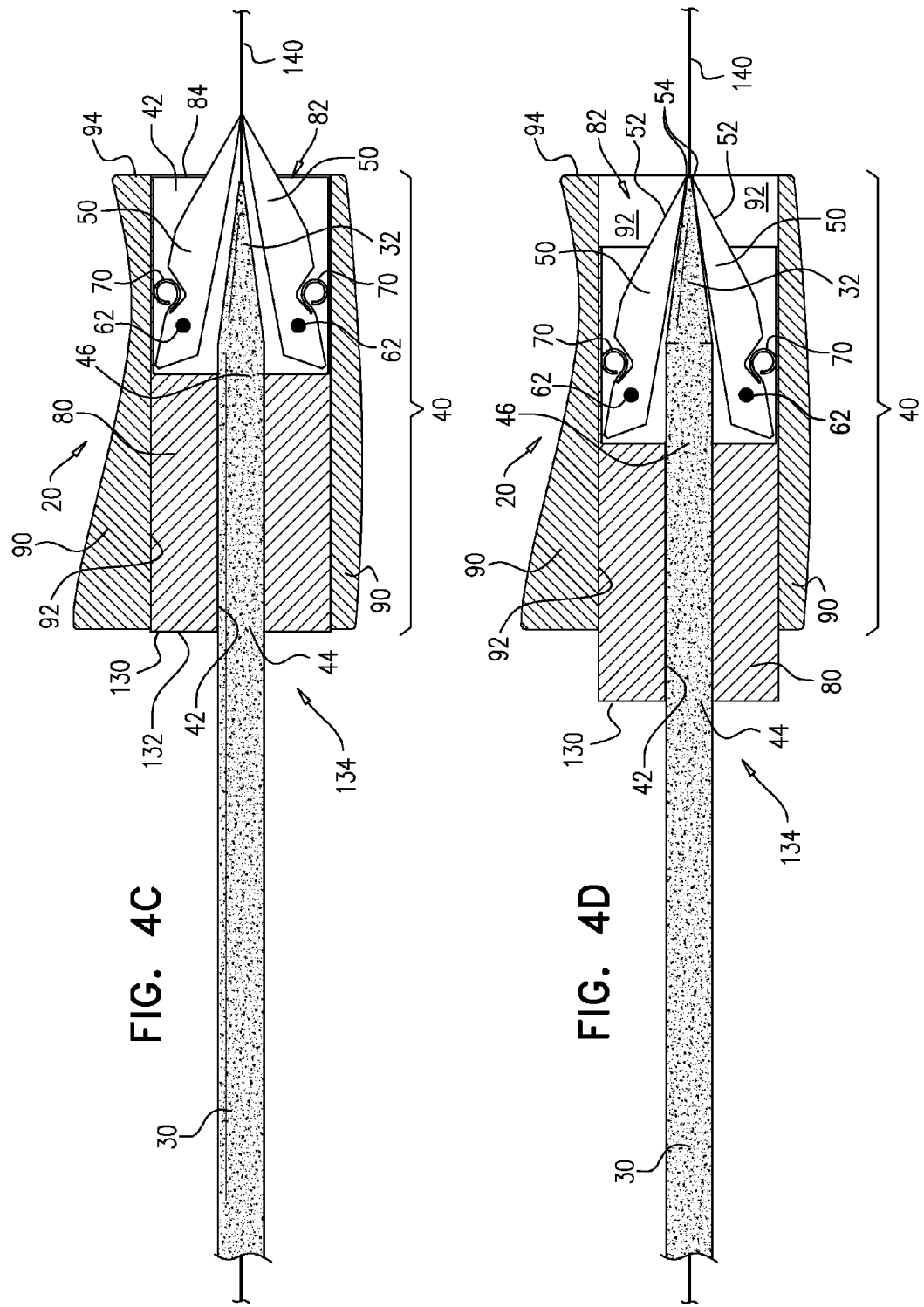

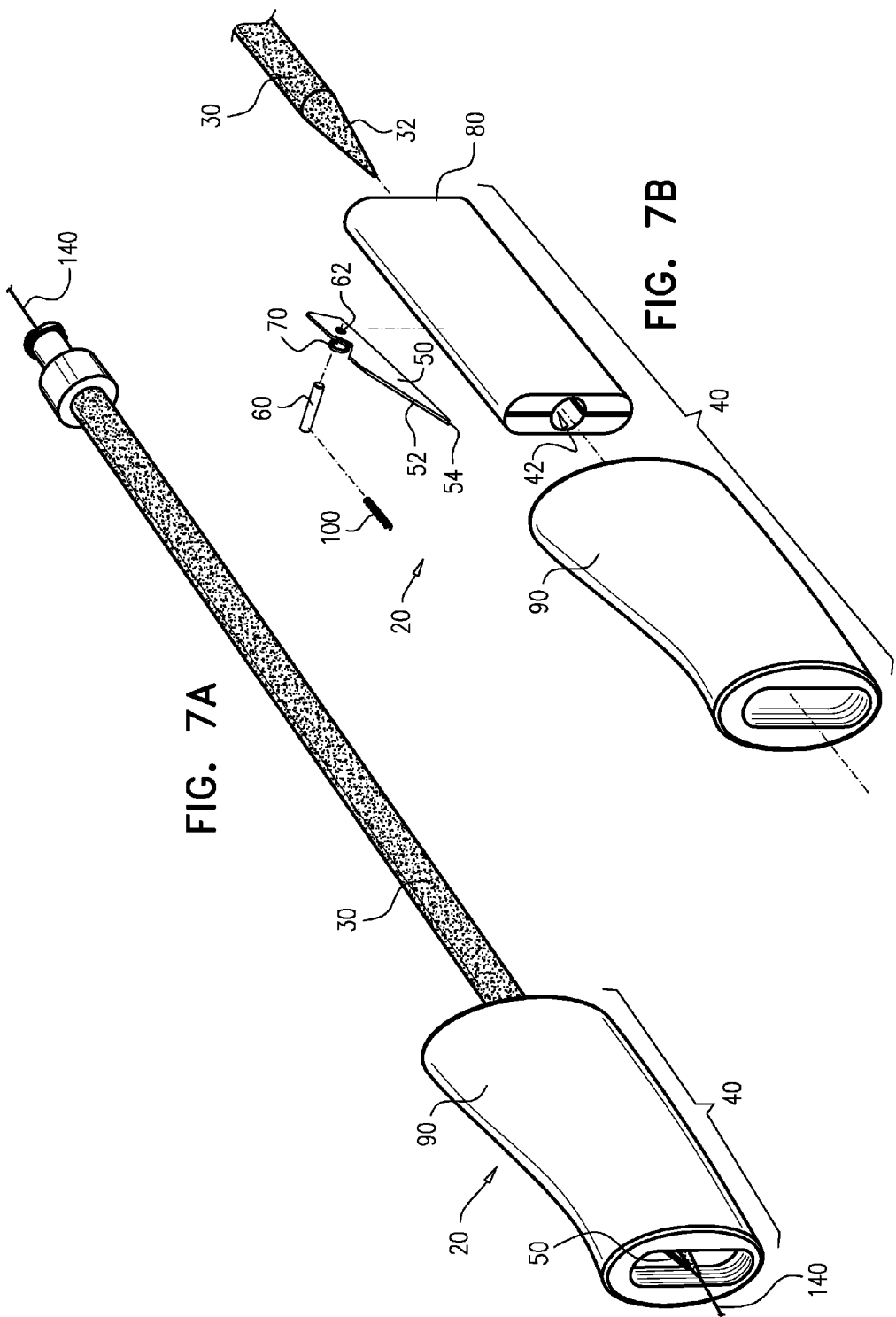

TISSUE CUTTER

FIELD OF THE APPLICATION

The present invention relates generally to surgical devices and techniques, and specifically to surgical devices and techniques for cutting tissue.

BACKGROUND OF THE APPLICATION

The Seldinger technique is a medical procedure for providing safe access to blood vessels and other anatomic sites. The skin is punctured with a sharp hollow needle. A guidewire is then advanced through the lumen of the needle, and the needle is withdrawn. A small skin incision is made into the skin at the entry site of the wire. A hollow tubular element, such as a sheath, is passed over the guidewire into the target anatomic location, and the guidewire is withdrawn.

SUMMARY OF THE APPLICATION

In embodiments of the present invention, a tissue cutter is provided for use with a hollow tubular element having a tapered distal portion. The tissue cutter is used to make an incision in tissue, such as skin, for subsequent insertion of the hollow tubular element through the incision. For example, the tissue cutter may be used for making an incision during performance of the Seldinger technique.

The tissue cutter typically comprises:
- a housing, which is shaped so as to define a longitudinal hollow-tubular-element-accepting channel that is shaped for slidable passage therethrough of the hollow tubular element, and has a central longitudinal axis;
- one or more blades, each of which extends alongside the central longitudinal axis, and defines a sharp cutting surface that reaches a distal-most point of the blade and faces away from the central longitudinal axis;
- one or more pivots, each of which couples one of the blades to the housing such that the blade is rotatable with respect to the housing around a pivot point of the blade; and
- one or more blade springs, each of which is arranged to apply a force to one of the blades that pushes a distal portion of the blade against the tapered distal portion of the hollow tubular element when the blade is positioned alongside the tapered distal portion.

The longitudinal hollow-tubular-element-accepting channel holds the hollow tubular element at the appropriate alignment with respect to the one or more blades.

For some applications, the housing comprises a radially-inner structure and an outer finger shield. The radially-inner structure is shaped so as to define longitudinal hollow-tubular-element-accepting channel. The one or more pivots couple the one or more blades to the radially-inner structure. A protruding distal segment of each of the one or more blades protrudes distally beyond a distal end of the radially-inner structure. The finger shield is shaped so as to define a longitudinal inner-structure-accepting channel that is shaped for slidable disposition therein of the radially-inner structure.

For some applications, the finger shield is configured to assume:
- a shielding state, in which (a) a distal end of the finger shield is disposed more distally than the distal end of the radially-inner structure, and (b) a portion of the finger shield surrounds at least a longitudinal part of the protruding distal segments of the one or more blades (e.g., completely radially surrounds at least a longitudinal part of the protruding distal segment of the one or more blades), and
- a non-shielding state, in which (a) the distal end of the finger shield is disposed more proximally than when in the shielding state, and (b) the finger shield surrounds longitudinally less of the protruding distal segments of the one or more blades than when in the shielding state.

For some applications, the tissue cutter further comprises one or more finger-shield springs, which, when loaded, are arranged to push the finger shield distally with respect to the radially-inner structure. For some of these applications, the pivots (a) extend radially out of the radially-inner structure and into a wall of the finger shield, and (b) are distally and proximally slidable within the wall of the finger shield. The finger-shield springs, when loaded, are arranged to push the finger shield distally with respect to the radially-inner structure via the respective pivots.

Typically, the tissue cutter further comprises a user control button, which is configured, upon depression of thereof, to advance the radially-inner structure distally with respect to the finger shield.

In some applications of the present invention, the cutter tool is used to perform the Seldinger technique. A hollow needle is inserted through an entry site on an external surface of the skin, through tissue, and into a target anatomic site, such as a blood vessel (a vein or an artery), generally under ultrasound guidance, as is known in the art. A distal portion of a guidewire is placed through the entry site, via the needle, into the blood vessel, such that a proximal portion of the guidewire remains outside the skin, as is known in the art.

The tissue cutter, with the hollow tubular element inserted in the longitudinal inner-structure-accepting channel, is guided distally over the proximal portion of the guidewire, typically while (a) the hollow tubular element is disposed in the longitudinal hollow-tubular-element-accepting channel with the one or more blades positioned alongside the tapered distal portion, (b) the one or more blade springs apply the force(s) to the blade(s) that push the distal portion(s) of the blade(s) against the tapered distal portion of the hollow tubular element, and (c) the guidewire passes through a longitudinal guidewire-accepting channel defined by the hollow tubular element. At this stage of the procedure, the finger shield is in the shielding state, in which it surrounds the blades.

The tissue cutter, with the hollow tubular element therein, is advanced to the outer surface of the skin, until the tapered distal portion and the distal end of the housing contact the external surface of the skin, and, typically, are pressed against the external surface of the skin. As mentioned above, the longitudinal hollow-tubular-element-accepting channel holds the hollow tubular element at the appropriate alignment with respect to the one or more blades. As a result, the guidewire guides the hollow tubular element to the entry site on the skin (while the surgeon is careful not to kink the guidewire), and the hollow tubular element in turn guides the blades to the entry site on the skin.

The surgeon depresses the user control button, which causes the blades to protrude from the finger shield, distally advance into the skin, and make an incision through the skin. At this stage of the procedure, the hollow tubular element typically remains within the finger shield, such that the blades protrude distally beyond the distal end of the hollow tubular element. The tissue cutter ensures that the incision is made away from the guidewire, in order to avoid damaging the guidewire at its insertion point into the skin. The tissue cutter also ensures that the guidewire is actually within the incision, and not separated from the incision by a tag of skin.

The surgeon releases the user control button, such that the finger-shield springs return the finger shield to the shielding state. In addition, the surgeon proximally withdraws the tissue cutter over the proximal portion of the guidewire, such that the hollow tubular element remains touching the outer surface of the skin. The hollow tubular element is advanced through the incision, as is known in the art.

There is therefore provided, in accordance with an application of the present invention, apparatus for use with a hollow tubular element having a tapered distal portion, the apparatus including a tissue cutter, which includes:

a housing, which is shaped so as to define a longitudinal hollow-tubular-element-accepting channel that is shaped for slidable disposition therein of the hollow tubular element, and has proximal and distal openings and a central longitudinal axis;

a blade, which extends alongside the central longitudinal axis, and defines a sharp cutting surface that reaches a distal-most point of the blade and faces away from the central longitudinal axis;

a pivot, which couples the blade to the housing such that the blade is rotatable with respect to the housing around a pivot point of the blade; and a blade spring, which is arranged to apply a force to the blade that pushes a distal portion of the blade against the tapered distal portion of the hollow tubular element when the blade is positioned alongside the tapered distal portion.

For some applications, the blade is a first blade, the sharp cutting surface is a first sharp cutting surface, the distal-most point of the blade is a first distal-most point of the blade, the pivot is a first pivot, the pivot point is a first pivot point, the blade spring is a first blade spring, the force is a first force, the distal portion of the blade is a first distal portion of the blade, and the tissue cutter further includes:

a second blade, which extends alongside the central longitudinal axis, and defines a second sharp cutting surface that reaches a second distal-most point of the second blade and faces away from the central longitudinal axis in a second radial direction different from a first radial direction in which the first sharp cutting surface faces;

a second pivot, which couples the second blade to the housing such that the second blade is rotatable with respect to the housing around a second pivot point of the second blade; and a second blade spring, which is arranged to apply a second force to the second blade that pushes a second distal portion of the second blade against the tapered distal portion of the hollow tubular element when the second blade is positioned alongside the tapered distal portion.

For some applications, the first and the second blades rotate around the first and the second pivot points, respectively, by respective angles of between 1 and 45 degrees during a transition between (a) a first state in which the hollow tubular element holds the first and the second blades a distance apart and (b) a second state in which the hollow tubular element is not positioned alongside the first and the second blades, the distance equal to 95% of an inner diameter of the longitudinal hollow-tubular-element-accepting channel.

For some applications, the longitudinal hollow-tubular-element-accepting channel has a smallest inner diameter of between 1.67 mm and 3 cm.

For some applications, the housing includes:

a radially-inner structure, which is shaped so as to define the longitudinal hollow-tubular-element-accepting channel, wherein the pivot couples the blade to the radially-inner structure, and wherein a protruding distal segment of the blade protrudes distally beyond a distal end of the radially-inner structure; and an outer finger shield, which is shaped so as to define a longitudinal radially-inner-structure-accepting channel that is shaped for slidable disposition therein of the radially-inner structure.

For some applications, the finger shield is configured to assume:

a shielding state, in which (a) a distal end of the finger shield is disposed more distally than the distal end of the radially-inner structure, and (b) a portion of the finger shield surrounds at least a longitudinal part of the protruding distal segment of the blade, and a non-shielding state, in which (a) the distal end of the finger shield is disposed more proximally than when in the shielding state, and (b) the finger shield surrounds longitudinally less of the protruding distal segment of the blade than when in the shielding state.

For some applications, the finger shield is configured such that when the finger shield is in the shielding state, the portion of the finger shield completely radially surrounds the at least a longitudinal part of the protruding distal segment of the blade.

For some applications, the tissue cutter further includes a finger-shield spring, which is arranged to push the finger shield distally with respect to the radially-inner structure.

For some applications:

the pivot (a) extends radially out of the radially-inner structure and into a wall of the finger shield, and (b) is distally and proximally slidable within the wall of the finger shield, and the finger-shield spring, when loaded, is arranged to push the finger shield distally with respect to the radially-inner structure via the pivot.

For some applications, the tissue cutter further includes a user control button, which is configured, upon depression of thereof, to advance the radially-inner structure distally with respect to the finger shield.

For some applications, the user control button is shaped so as to define a surface that is accessible from a proximal end of the housing.

For some applications, the blade is sterile. Alternatively or additionally, for some applications, the tissue cutter is sterile.

For some applications, a kit is provided, which includes the tissue cutter and the hollow tubular element. For some applications, the kit further includes a guidewire, and the hollow tubular element is shaped so as to define a longitudinal guidewire-accepting channel therethrough that is sized to accept the guidewire.

There is further provided, in accordance with an application of the present invention, a method including:

providing (a) a guidewire, (b) a hollow tubular element having a tapered distal portion, and shaped so as to define a longitudinal guidewire-accepting channel, and (c) a tissue cutter, which includes:

a housing, which is shaped so as to define a longitudinal hollow-tubular-element-accepting channel that is shaped for slidable disposition therein of the hollow tubular element, and has proximal and distal openings and a central longitudinal axis;

a blade, which extends alongside the central longitudinal axis, and defines a sharp cutting surface that reaches a distal-most point of the blade and faces away from the central longitudinal axis;

a pivot, which couples the blade to the housing such that the blade is rotatable with respect to the housing around a pivot point of the blade; and a blade spring, which is arranged to apply a force to the blade that pushes a distal portion of the blade against the tapered distal portion of the hollow tubular element when the blade is positioned alongside the tapered distal portion;

placing a distal portion of the guidewire through an entry site on an external surface of skin of a subject and into an anatomic site, such that a proximal portion of the guidewire remains outside the skin;

guiding the hollow tubular element and the tissue cutter over the proximal portion of the guidewire, until the tapered distal portion of the hollow tubular element and a distal end of the housing contact the external surface of the skin, while (a) the hollow tubular element is disposed in the longitudinal hollow-tubular-element-accepting channel with the blade positioned alongside the tapered distal portion, (b) the blade spring applies the force to the blade that pushes the distal portion of the blade against the tapered distal portion of the hollow tubular element, and (c) the guidewire is disposed in the longitudinal guidewire-accepting channel;

thereafter, making an incision in the skin at the entry site by distally advancing the blade into the skin;

and thereafter, advancing the hollow tubular element through the incision.

For some applications, making the incision includes distally advancing the blade into the skin while holding the hollow tubular element axially stationary.

For some applications, the method further includes proximally withdrawing the tissue cutter after making the incision and before advancing the hollow tubular element through the incision.

For some applications, the blade is a first blade, the sharp cutting surface is a first sharp cutting surface, the distal-most point of the blade is a first distal-most point of the blade, the pivot is a first pivot, the pivot point is a first pivot point, the blade spring is a first blade spring, the force is a first force, the distal portion of the blade is a first distal portion of the blade, and the tissue cutter further includes:

a second blade, which extends alongside the central longitudinal axis, and defines a second sharp cutting surface that reaches a second distal-most point of the second blade and faces away from the central longitudinal axis in a second radial direction different from a first radial direction in which the first sharp cutting surface faces;

a second pivot, which couples the second blade to the housing such that the second blade is rotatable with respect to the housing around a second pivot point of the second blade; and a second blade spring, which is arranged to apply a second force to the second blade that pushes a second distal portion of the second blade against the tapered distal portion of the hollow tubular element when the second blade is positioned alongside the tapered distal portion, and making the incision includes making the incision in the skin by distally advancing the first and the second blades into the skin.

For some applications, the first and the second blades rotate around the first and the second pivot points, respectively, by respective angles of between 1 and 45 degrees during a transition between (a) a first state in which the hollow tubular element holds the first and the second blades a distance apart and (b) a second state in which the hollow tubular element is not positioned alongside the first and the second blades, the distance equal to 95% of an inner diameter of the longitudinal hollow-tubular-element-accepting channel.

For some applications, the longitudinal hollow-tubular-element-accepting channel has a smallest inner diameter of between 1.67 mm and 3 cm.

For some applications, the housing includes:

a radially-inner structure, which is shaped so as to define the longitudinal hollow-tubular-element-accepting channel, wherein the pivot couples the blade to the radially-inner structure, and wherein a protruding distal segment of the blade protrudes distally beyond a distal end of the radially-inner structure; and an outer finger shield, which is shaped so as to define a longitudinal radially-inner-structure-accepting channel that is shaped for slidable disposition therein of the radially-inner structure.

For some applications:

guiding includes guiding the hollow tubular element and the tissue cutter over the proximal portion of the guidewire while the finger shield is in a shielding state, in which (a) a distal end of the finger shield is disposed more distally than the distal end of the radially-inner structure, and (b) a portion of the finger shield surrounds at least a longitudinal part of the protruding distal segment of the blade, and making the incision includes transitioning the finger shield to a non-shielding state, in which (a) the distal end of the finger shield is disposed more proximally than when in the shielding state, and (b) the finger shield surrounds longitudinally less of the protruding distal segment of the blade than when in the shielding state.

For some applications, the finger shield is configured such that when the finger shield is in the shielding state, the portion of the finger shield completely radially surrounds the at least a longitudinal part of the protruding distal segment of the blade.

For some applications, the tissue cutter further includes a finger-shield spring, which is arranged to push the finger shield distally with respect to the radially-inner structure.

For some applications:

the pivot (a) extends radially out of the radially-inner structure and into a wall of the finger shield, and (b) is distally and proximally slidable within the wall of the finger shield, and the finger-shield spring, when loaded, is arranged to push the finger shield distally with respect to the radially-inner structure via the pivot.

For some applications:

the tissue cutter further includes a user control button, which is configured, upon depression of thereof, to advance the radially-inner structure distally with respect to the finger shield, and making the incision includes depressing the user control button.

For some applications:

the user control button is shaped so as to define a surface that is accessible from a proximal end of the housing, and making the incision includes depressing the surface of the user control button that is accessible from the proximal end of the housing.

The present invention will be more fully understood from the following detailed description of embodiments thereof, taken together with the drawings, in which:

BRIEF DESCRIPTION OF THE DRAWINGS

FIGS. 1A-B are schematic illustrations of a tissue cutter and a hollow tubular element, in accordance with an application of the present invention;

FIG. 2 is an exploded view of the tissue cutter and the hollow tubular element of FIGS. 1A-B, in accordance with an application of the present invention;

FIGS. 4A-D are schematic illustrations showing the operation of the tissue cutter of FIGS. 1A-3B, in accordance with an application of the present invention;

FIGS. 7A-B are schematic illustrations of another configuration of the tissue cutter of FIGS. 1A-4B, in accordance with an application of the present invention.

DETAILED DESCRIPTION OF APPLICATIONS

Figure 3A:
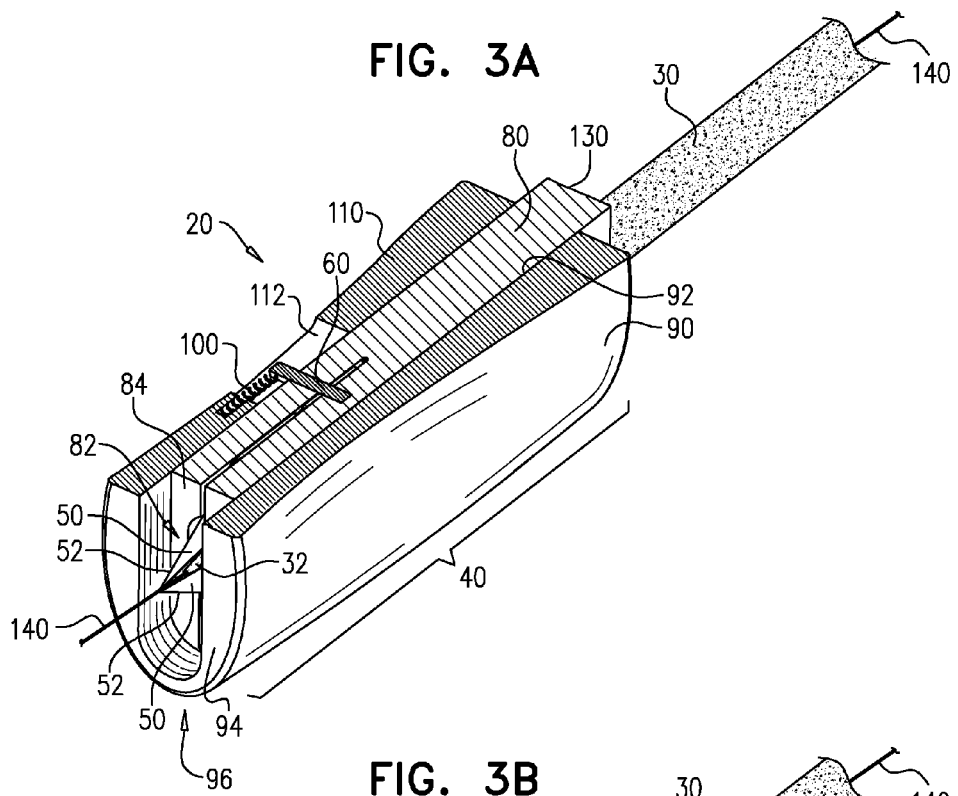
FIGS. 3A-B are partial cross-sectional views of the tissue cutter and the hollow tubular element of FIGS. 1A-B, in accordance with an application of the present invention.

FIGS. 1A-B and 2 are schematic illustrations of a tissue cutter 20 and an elongate hollow tubular element 30, in accordance with an application of the present invention. FIGS. 1A-B are two views of tissue cutter 20 fully assembled with hollow tubular element 30 inserted therein, and FIG. 2 is an exploded view of tissue cutter and hollow tubular element 30. Tissue cutter 20 is used to make an incision in tissue, such as skin, for subsequent insertion of hollow tubular element 30 through the incision. For example, tissue cutter 20 may be used for making an incision during performance of the Seldinger technique. Hollow tubular element 30 may comprise, for example, a dilator, a trocar, an endoscope, a catheter, a cannula, or a sheath. Hollow tubular element 30 typically has a tapered distal portion 32. FIGS. 1A-B also show a guidewire 140, which is disposed in a longitudinal guidewire-accepting channel defined by hollow tubular element 30, as is known in the art. Guidewire 140 typically has a blunt and/or round distal tip.

Tissue cutter 20 comprises:
- a housing 40, which is shaped so as to define a longitudinal hollow-tubular-element-accepting channel 42 that is shaped for slidable disposition therein of hollow tubular element 30, and has proximal and distal openings 44 and 46 (labeled in FIGS. 4A-D) and a central longitudinal axis 48 (labeled in FIG. 2);
- one or more blades 50, each of which extends alongside central longitudinal axis 48, and defines a sharp cutting surface 52 that reaches a distal-most point 54 of blade 50 and faces away from central longitudinal axis 48;
- one or more pivots 60, each of which couples one of blades 50 to housing 40 such that the blade is rotatable with respect to the housing around a pivot point 62 of the blade; and
- one or more blade springs 70, each of which is arranged to apply a force to one of blades 50 that pushes a distal portion 72 of the blade against tapered distal portion 32 of hollow tubular element when the blade is positioned alongside the tapered distal portion, such as shown in FIGS. 1A, 3A-B, and 4B.

As used in the present application, including in the claims, a "pivot" is a short rod, shaft, or pin on which a related part rotates. As used in the present application, including in the claims, "proximal" means toward the surgeon, and "distal" means away from the surgeon, toward the far end of tissue cutter 20.

Longitudinal hollow-tubular-element-accepting channel 42 holds hollow tubular element 30 at the appropriate alignment with respect to the one or more blades 50. To this end, hollow-tubular-element-accepting channel 42 is typically provided with a smallest inner diameter D (labeled in FIG. 4A) that is only slightly larger than the greatest outer diameter of hollow tubular element 30 (e.g., is less than 25% larger, such as less than 20% larger, e.g., less than 10% larger), such that hollow tubular element 30 fits snugly within the channel and is held in the proper alignment. For some applications, longitudinal hollow-tubular-element-accepting channel 42 has a smallest inner diameter D of at least 0.5 mm, no more than 3 cm, and/or between 0.5 and 3 cm, depending on the size of the hollow tubular element for which tissue cutter 20 is configured.

For some applications, tissue cutter 20 comprises exactly two blades 50, exactly two pivots 60, and exactly two blade springs 70, such as shown in FIGS. 1A-6G. In these applications, sharp cutting surfaces 52 face away from central longitudinal axis 48 in radial directions different from each other. Typically, pivot points 62 are equidistant from central longitudinal axis 48.

For other applications, tissue cutter 20 comprises exactly one blade 50, exactly one pivot 60, and exactly one blade spring 70, such as described hereinbelow with reference to FIGS. 7A-B. For still other applications, tissue cutter 20 comprises more than two blades, more than two pivots 60, and more than two blade springs 70, such as three or four of each of these elements (configurations not shown).

For some applications, blade springs 70 are fixed to or integral with respective blades 50. For some applications, as shown, blade springs 70 comprise respective torsion springs (to which a torque or twisting force is applied, causing the spring to rotate through an angle, as described hereinbelow). For other applications (configuration not shown), blade springs 70 comprise respective compression springs (to which an axial force is applied, causing the springs to become shorter).

For some applications, the one or more blade springs are arranged to apply respective radially-inwardly-directed forces against respective sites on blades 50 that are distal to respective pivot points 62, such as shown in the figures. For other applications, the one or more blade springs 70 are arranged to apply respective radially-outwardly-directed forces against respective sites on blades 50 that are proximal to respective pivot points 62 (configuration not shown.

Figure 3B:
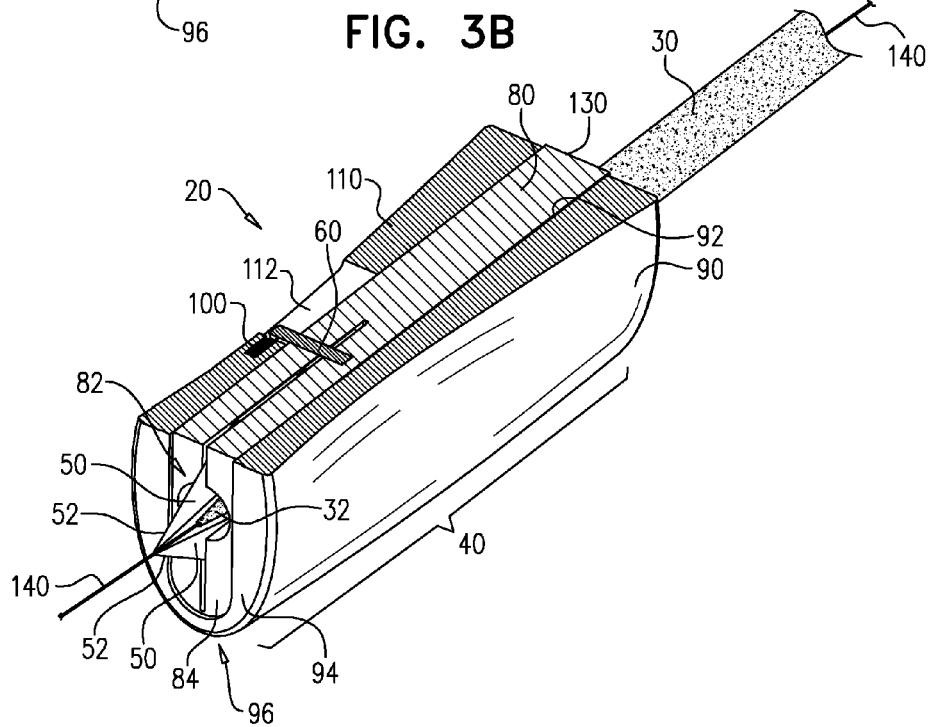
Figure 5:
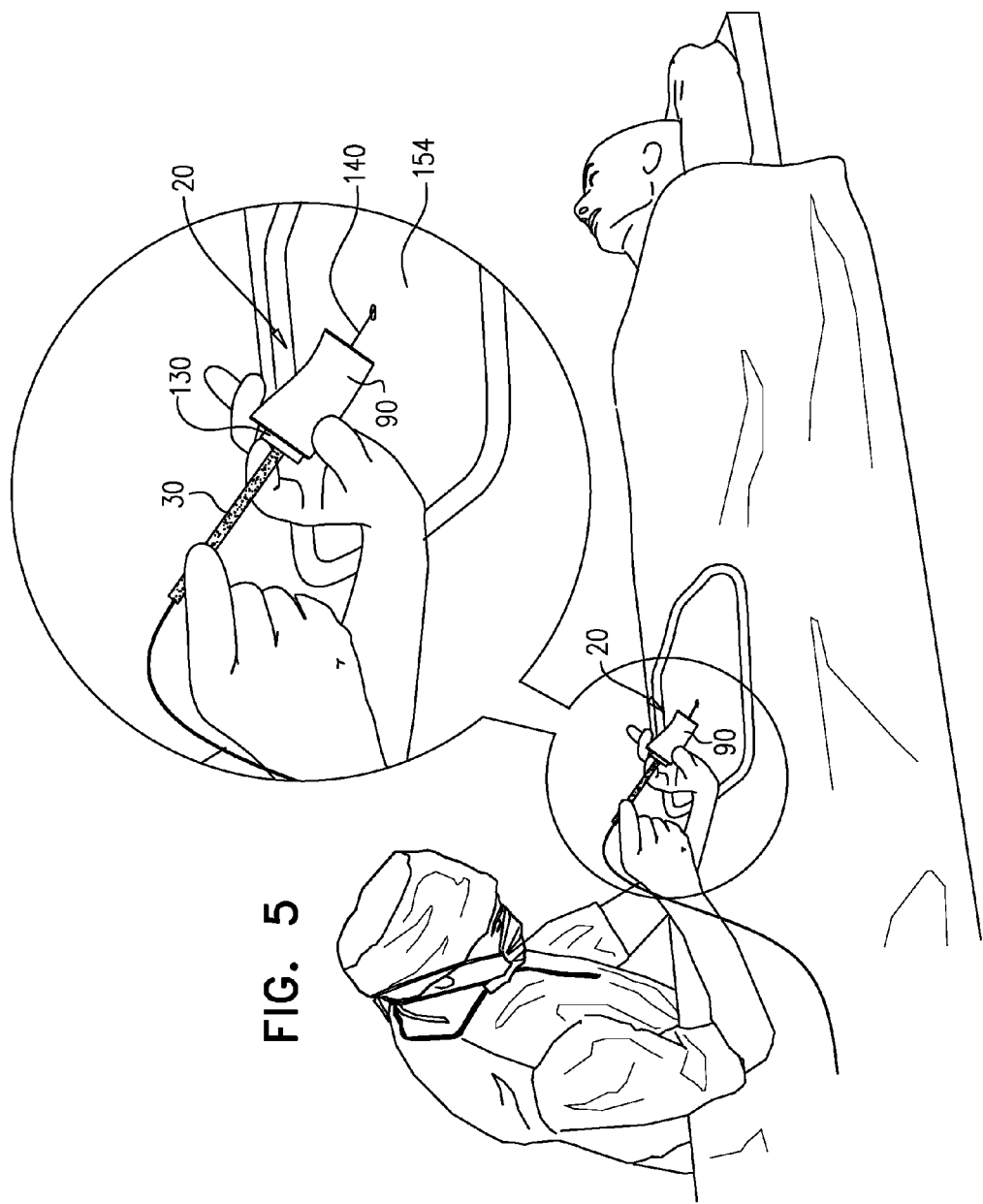
FIGS. 5 and 6A-J are schematic illustrations of the performance of the Seldinger technique using the tissue cutter of FIGS. 1A-4D, in accordance with an application of the present invention.

Reference is now made to FIGS. 3A-B, which are partial cross-sectional views of tissue cutter 20 and hollow tubular element 30, in accordance with an application of the present invention. For some applications, housing 40 comprises a radially-inner structure 80 and an outer finger shield 90. Radially-inner structure 80 is shaped so as to define longitudinal hollow-tubular-element-accepting channel 42. The one or more pivots 60 couple the one or more blades 50 to radially-inner structure 80. A protruding distal segment 82 of each of the one or more blades protrudes distally beyond a distal end 84 of radially-inner structure 80. Finger shield 90 is shaped so as to define a longitudinal inner-structure-accepting channel 92 that is shaped for slidable disposition therein of radially-inner structure 80.

For some applications, finger shield 90 is configured to assume:
- a shielding state, as shown in FIG. 3A (and in FIGS. 1A-B, 4A-B, 4D, 6C-D, and 6F-G), in which (a) a distal end 94 of finger shield 90 is disposed more distally than distal end 84 of radially-inner structure 80, and (b) a portion of finger shield 90 surrounds at least a longitudinal part of protruding distal segments 82 of the one or more blades 50 (e.g., completely radially surrounds at least a longitudinal part of the protruding distal segment of the one or more blades), and
- a non-shielding state, as shown in FIG. 3B (and in FIGS. 4C and 6E), in which (a) distal end 94 of finger shield 90 is disposed more proximally than when in the shielding state, and (b) finger shield 90 surrounds longitudinally less of protruding distal segments 82 of the one or more blades 50 than when in the shielding state.

Typically, when finger shield 90 is in the shielding state, distal end 94 of finger shield 90 is disposed at least 1 cm more distally than distal end 84 of radially-inner structure 80. For some applications, when finger shield 90 is in the shielding state, distal end 94 of finger shield 90 is disposed more distally than distal end 84 of radially-inner structure 80 than shown in FIG. 3A.

Typically, when finger shield 90 is in the shielding state, distal end 94 of finger shield 90 is disposed at least as distal as distal-most points 54 of blades 50. For some applications, distal end 94 of finger shield 90 is disposed between 0 and 20 mm (e.g., between 0 and 15 mm, such as between 5 and 15 mm, and/or at least 5 mm) more distal than distal-most points 54 of blades 50.

For some applications, finger shield 90 comprises a transparent or translucent material.

It is noted that the shielding state does not provide complete shielding, at least because the blades are typically still accessible from a distal end 96 of housing 40 even when the finger shield is in the shielding state. In addition, although the finger shield is shown as providing complete lateral shielding in the shielding state, this is not necessarily the case. Similarly, the finger shield still may provide some lateral shielding even when in the non-shielding state, even though the finger shield provides less lateral shielding when in the non-shielding state than when in the shielding state. Moreover, tissue cutter 20 is designed such that the one or more blades 50 are not exposed to the surgeon's fingers even when the finger shield is in the non-shielding state, because the blades are inserted in tissue of the subject when in this state, such as shown in FIG. 6E.

For some applications, tissue cutter 20 further comprises one or more finger-shield springs 100, which, when loaded, as shown in FIG. 3B, are arranged to push finger shield 90 distally with respect to radially-inner structure 80. For some of these applications, pivots 60 (a) extend radially out of radially-inner structure 80 and into a wall 110 of finger shield 90, and (b) are distally and proximally slidable within wall 110 of finger shield 90. Finger-shield springs 100, when loaded, as shown in FIG. 3B, are arranged to push finger shield 90 distally with respect to radially-inner structure 80 via respective pivots 60. To allow such extension of the pivots into wall 110, the wall is shaped so as to define cavities 112, which optionally extend entirely through wall 110 to an outer surface of finger shield 90, such as shown in FIGS. 3A-B and 1B). Alternatively, the cavities do not extend to the outer surface of the finger shield (configuration not shown). For some applications, finger-shield springs 100 directly contact respective pivots 60, as shown in FIGS. 3A-B (see also FIG. 2), while for other applications, one or more intermediate elements couple the finger-shield springs to the respective pivots.

For some applications, each of pivots 60 extends radially out of radially-inner structure 80 and into wall 110 of finger shield 90 at two sites of the wall on opposite sides of finger shield 90 (configuration not shown). For these applications, tissue cutter 20 typically comprises two finger-shield springs 100 for each pivot.

Typically, tissue cutter 20 further comprises a user control button 130, which is configured, upon depression of thereof, to advance radially-inner structure 80 distally with respect to finger shield 90. Typically, user control button 130 is shaped so as to define a surface 132 that is accessible from a proximal end 134 of housing 40 (labeled in FIG. 4C).

Reference is now made to FIGS. 4A-D, which are schematic illustrations showing the operation of tissue cutter 20, in accordance with an application of the present invention. FIGS. 4A-D show four states of tissue cutter 20 achieved during typical preparation and usage of the tool. FIG. 4A shows tissue cutter 20 and hollow tubular element 30 before insertion of hollow tubular element 30 into longitudinal hollow-tubular-element-accepting channel 42 of housing 40. FIGS. 4A-D also show guidewire 140, which is disposed in the longitudinal guidewire-accepting channel defined by hollow tubular element 30.

In the state shown in FIG. 4A, blade springs 70 typically push distal portions 72 of blades 50 (typically distal-most points 54 of blades 50) into direct contact with each other (guidewire 140 generally does not interfere with such contact). Typically longitudinal hollow-tubular-element-accepting channel 42 and blades 50 are aligned such that the blades contact each other at central longitudinal axis 48 of longitudinal hollow-tubular-element-accepting channel 42 (labeled in FIG. 2). As can be seen in FIG. 4B, longitudinal hollow-tubular-element-accepting channel 42 and blades 50 are aligned such that blades 50 come in direct contact with tapered distal portion 32 of hollow tubular element 30 when tapered distal portion 32 is disposed alongside blades 50. In the state shown in FIG. 4C, blade springs 70 typically push distal portions 72 of blades 50 (typically distal-most points 54 of blades 50) into direct contact with guidewire 140.

Reference is also made to FIGS. 5 and 6A-J, which are schematic illustrations of the performance of the Seldinger technique using tissue cutter 20, in accordance with an application of the present invention. In the illustrated Seldinger technique, hollow tubular element 30 typically comprises a dilator.

Figure 6A:
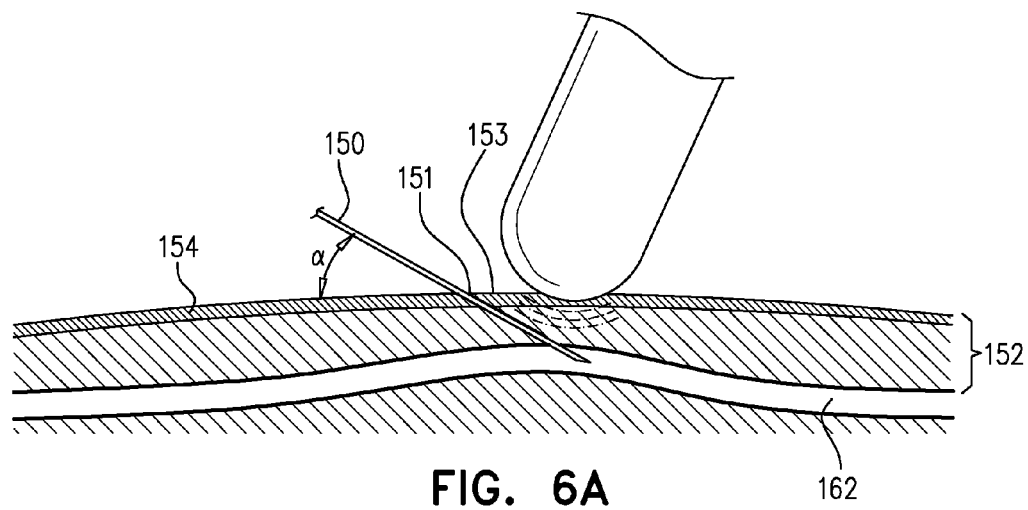

As shown in FIG. 6A, a hollow needle 150 (e.g., a trocar) is inserted through an entry site 151 on an external surface 153 of skin 154, through tissue 152, including skin 154, and into a target blood vessel 162 (a vein or an artery) or other anatomic site, generally under ultrasound guidance, as is known in the art. Needle 150 is typically oriented at an angle α (alpha) of less than 90 degrees with respect to an outer surface of skin 154.

Figure 6B:
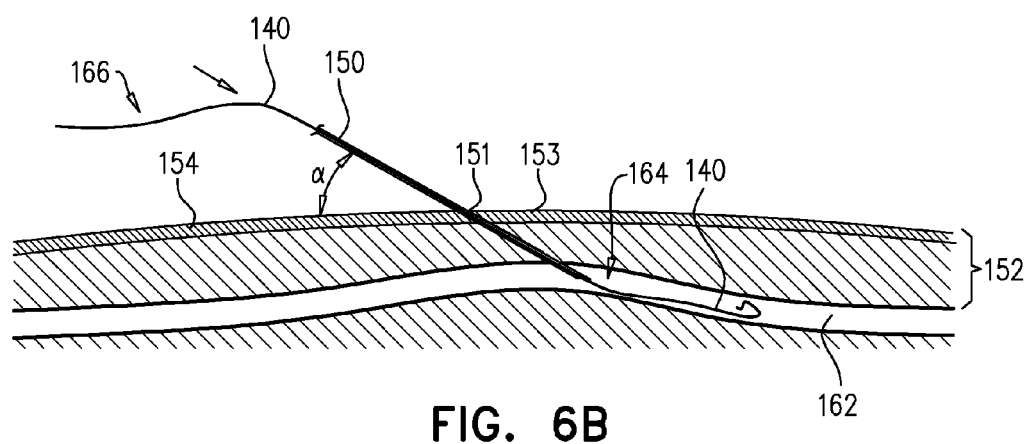

As shown in FIG. 6B, a distal portion 164 of guidewire 140 is placed through entry site 151, via needle 150, into blood vessel 162, such that a proximal portion 166 of the guidewire remains outside the skin, as is known in the art.

Figure 6C:
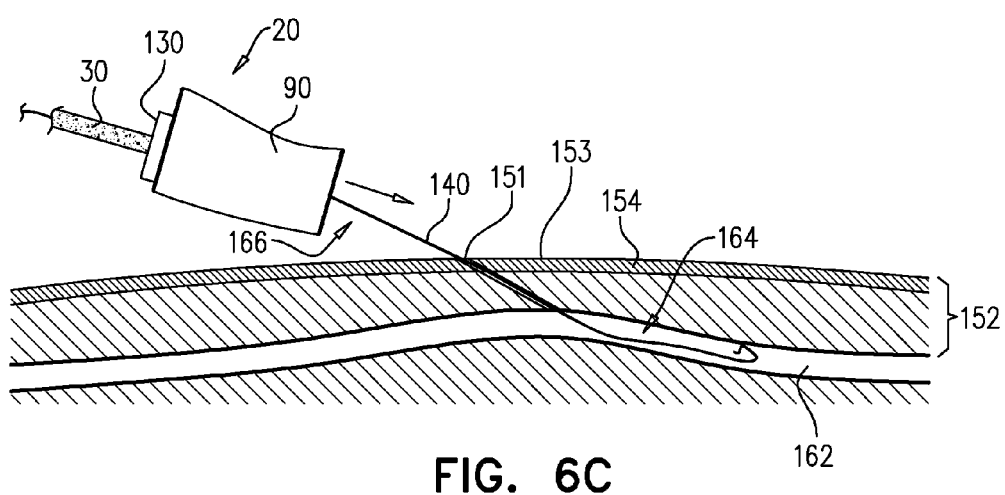

As is shown in FIG. 6C (and FIG. 5), tissue cutter 20, with hollow tubular element 30 inserted in longitudinal inner-structure-accepting channel 92 (labeled in FIGS. 3A-B and 4A-D), is guided distally over proximal portion 166 of guidewire 140 (i.e., longitudinal inner-structure-accepting channel 92 radially surrounds guidewire 140), typically while (a) hollow tubular element 30 is disposed in longitudinal hollow-tubular-element-accepting channel 42 with the one or more blades positioned alongside tapered distal portion 32, (b) the one or more blade springs 70 apply the force(s) to blade(s) 50 that push the distal portion(s) 72 of blade(s) 70 against tapered distal portion 32 of hollow tubular element 30, and (c) guidewire 140 is disposed in (and thus is radially surrounded by) the longitudinal guidewire-accepting channel defined by hollow tubular element 30. FIG. 4B shows tissue cutter 20, hollow tubular element 30, and guidewire 140 in the stage of deployment shown in FIG. 6C. As can be seen, at this stage of the procedure, finger shield 90 is in the shielding state, in which it surrounds blades 50. In addition, hollow tubular element 30 is also typically within finger shield 90, with the distal end of tapered distal portion 32 axially aligned with distal-most points 54 of blades 50. Alternatively, hollow tubular element 30 is first advanced to external surface 153 of skin 154, and tissue cutter 20 is then advanced distally over hollow tubular element 30. Further alternatively, tissue cutter 20 is first placed against external surface 153 of skin 154, and hollow tubular element 30 is then inserted through longitudinal hollow-tubular-element-accepting channel 42 of tissue cutter 20.

Figure 6D:
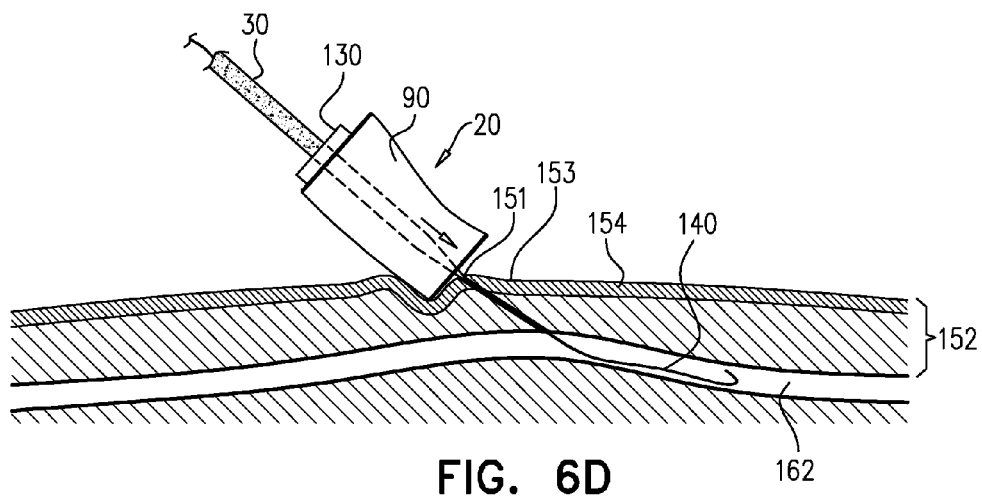
Figure 6E:
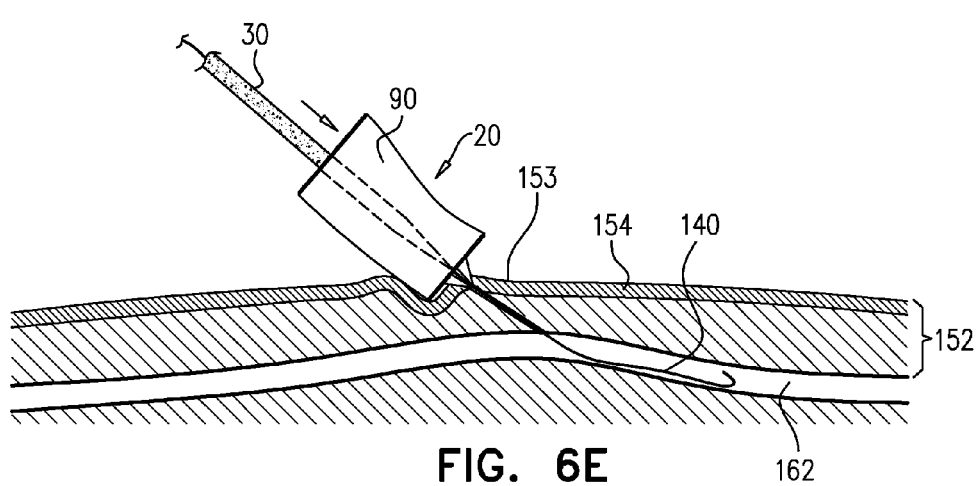

As is shown in FIG. 6D, tissue cutter 20, with hollow tubular element 30 therein, is advanced to the outer surface of skin 154, until tapered distal portion 32 and distal end 96 of housing 40 contact external surface 153 (typically at entry site 151), and, typically, are pressed against external surface 153 of skin 154. Tissue cutter 20 and hollow tubular element 30 are still in the stage of deployment shown in FIG. 4B. As mentioned above, longitudinal hollow-tubular-element-accepting channel 42 holds hollow tubular element 30 at the appropriate alignment with respect to the one or more blades 50. As a result, guidewire 140 guides hollow tubular element 30 to entry site 151 on the skin (while the surgeon is careful not to kink the guidewire), and hollow tubular element 30 in turn guides the blades to entry site 151 on the skin. Hollow tubular element 30 is typically oriented at the angle α (alpha) mentioned above.

As is shown in FIG. 6E, the surgeon depresses user control button 130, which causes blades 50 to protrude from finger shield 90, distally advance into the skin, and make an incision through skin 154 at entry site 151 (it is noted that in configurations in which tissue cutter 20 comprises a plurality of blades 50, typically the blades together make a single incision). FIG. 4C shows tissue cutter 20, hollow tubular element 30, and guidewire 140 in the stage of deployment shown in FIG. 6E. As can be seen, finger shield 90 is in the non-shielding state, in which blades 50 protrude distally from distal end 94 of finger shield 90. At this stage of the procedure, hollow tubular element 30 typically remains within finger shield 90, such that blades 50 protrude distally beyond the distal end of hollow tubular element 30. Typically, hollow tubular element 30 is held stationary as the blades are advanced into the skin. As a result, blade springs 70 typically push distal portions 72 of blades 50 (typically distal-most points 54 of blades 50) into direct contact with each other. Hollow tubular element 30 is typically oriented at the angle α (alpha) mentioned above.

Tissue cutter 20 ensures that the incision is made away from guidewire 140, in order to avoid damaging the guidewire at its insertion point into the skin. Tissue cutter 20 also ensures that guidewire 140 is actually within the incision, and not separated from the incision by a tag of skin.

Figure 6F:
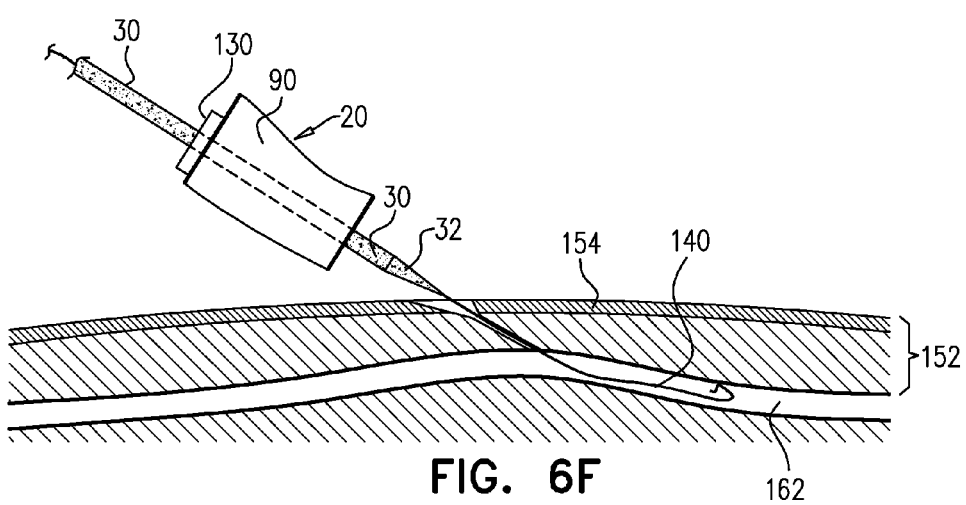

As is shown in FIG. 6F, the surgeon releases user control button 130, such that finger-shield springs 100 return finger shield 90 to the shielding state. In addition, the surgeon proximally withdraws tissue cutter 20 over proximal portion 166 of guidewire 140, such that hollow tubular element 30 remains touching the outer surface of skin 154. This stage of deployment is also shown in FIG. 4D.

Figure 6G:
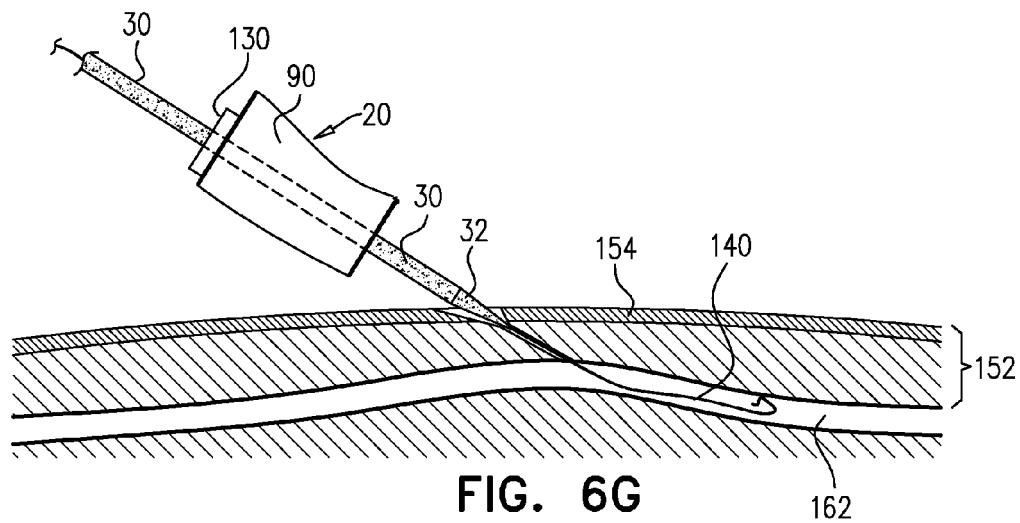

As shown in FIG. 6G, hollow tubular element 30 is advanced through the incision in skin 154.

Figure 6H:
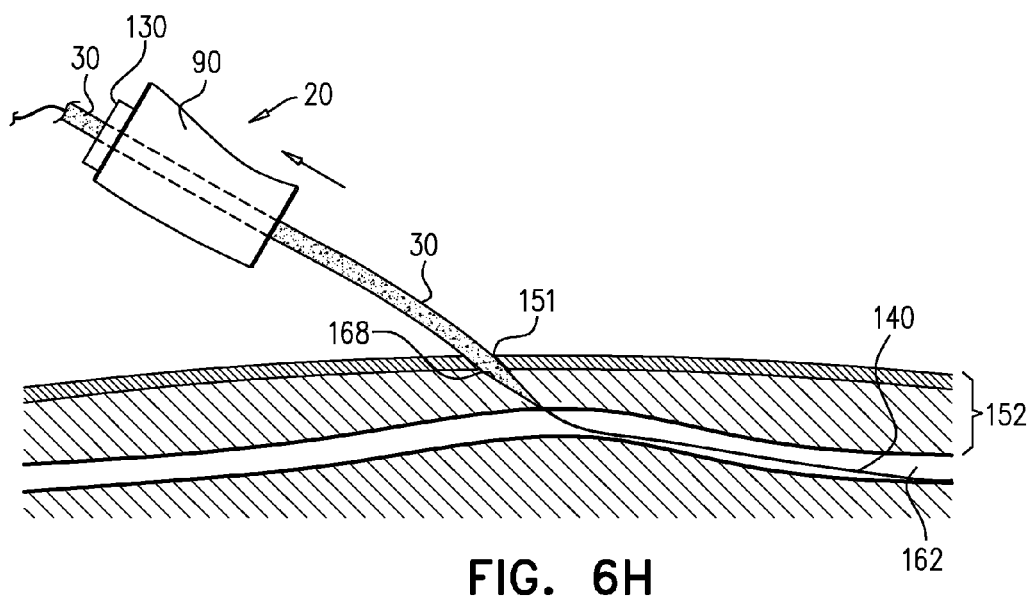

As shown in FIG. 6H, for applications in which hollow tubular element 30 comprises a dilator, such as shown, hollow tubular element 30 is advanced through the incision and tissue 152 (including skin 154), until tapered distal portion 32 reaches but does not penetrate the blood vessel 162, thereby creating a tunnel 168 from external surface 153 of skin 154 to blood vessel 162. For some other applications, such as in which hollow tubular element 30 comprises a catheter, the catheter is advanced into and along a portion of blood vessel 162 at this step of the procedure, as is known in the art.

Figure 6I:
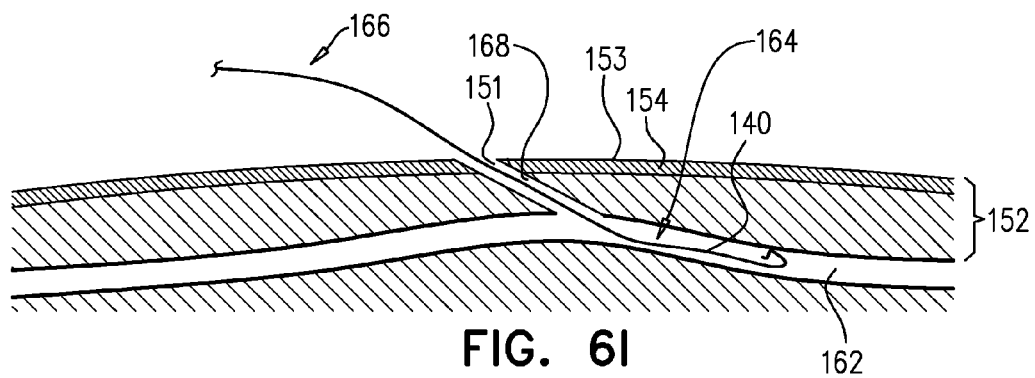

As shown in FIG. 6I, hollow tubular element 30 is removed from tunnel 168, while leaving guidewire 140 in place in blood vessel 162.

Figure 6J:
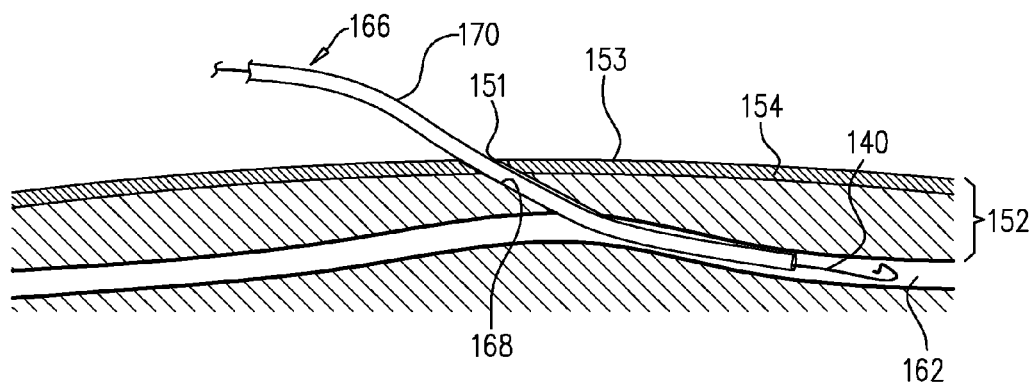

As shown in FIG. 6J, a catheter 170 is advanced over guidewire 140, through tunnel 168, and into blood vessel 162, as is known in the art. Guidewire 140 is withdrawn, thereby completing the Seldinger technique.

For some applications, a kit is provided that comprises tissue cutter 20, hollow tubular element 30, and, optionally, additional conventional elements used for performing the Seldinger technique, as known in the art, such as guidewire 140, hollow needle 150, and a syringe. Typically, tissue cutter 20, including blades 50, is sterile when provided to the surgeon.

Reference is made to FIGS. 4A and 6F. For some applications, blades 50 rotate around respective pivot points 62 by respective angles of between 0 and 90 degrees, e.g., between 5 and 90 degrees, such as between 5 and 45 degrees (e.g., between 1 and 45 degrees), during a transition between (a) a first state in which hollow tubular element 30 holds the blades a distance apart, as shown in FIG. 6F, and (b) a second state in which hollow tubular element 30 is not positioned alongside blades 50, as shown in FIG. 4A, the distance equal to 95% of an inner diameter of longitudinal hollow-tubular-element-accepting channel 42. As mentioned above, blades 50 typically directly contact each other when in the second state. Typically, the distance is at least 1.67 mm, no more than 3 cm, and/or between 1.67 mm and 3 cm, depending on the size of the hollow tubular element.

Reference is now made to FIGS. 7A-B, which are schematic illustrations of another configuration of tissue cutter 20, in accordance with an application of the present invention. In this configuration, tissue cutter 20 comprises exactly one blade 50, exactly one pivot 60, and exactly one blade spring 70.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for use with a hollow tubular element having a tapered distal portion, the apparatus comprising a tissue cutter, which comprises:
   a housing, which is shaped so as to define a longitudinal hollow-tubular-element-accepting channel that is shaped for slidable disposition therein of the hollow tubular element, and has proximal and distal openings and a central longitudinal axis;
a blade, which extends alongside the central longitudinal axis, and defines a sharp cutting surface that reaches a distal-most point of the blade and faces away from the central longitudinal axis;
a pivot, which couples the blade to the housing such that the blade is rotatable with respect to the housing around a pivot point of the blade; and
a blade spring, which is arranged to apply a force to the blade that pushes a distal portion of the blade against the tapered distal portion of the hollow tubular element when the blade is positioned alongside the tapered distal portion,
wherein the housing comprises:
a radially-inner structure, which is shaped so as to define the longitudinal hollow-tubular-element-accepting channel, wherein the pivot couples the blade to the radially-inner structure, and wherein a protruding distal segment of the blade protrudes distally beyond a distal end of the radially-inner structure; and
an outer finger shield, which is shaped so as to define a longitudinal radially-inner-structure-accepting channel that is shaped for slidable disposition therein of the radially-inner structure, and
wherein the tissue cutter further comprises a finger-shield spring, which is arranged to push the finger shield distally with respect to the radially-inner structure.

2. The apparatus according to claim 1,
wherein the blade is a first blade, the sharp cutting surface is a first sharp cutting surface, the distal-most point of the blade is a first distal-most point of the blade, the pivot is a first pivot, the pivot point is a first pivot point, the blade spring is a first blade spring, the force is a first force, and the distal portion of the blade is a first distal portion of the blade,
wherein the tissue cutter further comprises:
a second blade, which extends alongside the central longitudinal axis, and defines a second sharp cutting surface that reaches a second distal-most point of the second blade and faces away from the central longitudinal axis in a second radial direction different from a first radial direction in which the first sharp cutting surface faces;
a second pivot, which couples the second blade to the housing such that the second blade is rotatable with respect to the housing around a second pivot point of the second blade; and
a second blade spring, which is arranged to apply a second force to the second blade that pushes a second distal portion of the second blade against the tapered distal portion of the hollow tubular element when the second blade is positioned alongside the tapered distal portion,
wherein the first and the second pivots couple the first and the second blades, respectively, to the radially-inner structure, and
wherein protruding distal segments of the first and the second blades, respectively, protrude distally beyond the distal end of the radially-inner structure.

3. The apparatus according to claim 2, wherein the first and the second blades rotate around the first and the second pivot points, respectively, by respective angles of between 1 and 45 degrees during a transition between (a) a first state in which the hollow tubular element holds the first and the second blades a distance apart and (b) a second state in which the hollow tubular element is not positioned alongside the first and the second blades, the distance equal to 95% of an inner diameter of the longitudinal hollow-tubular-element-accepting channel.

4. The apparatus according to claim 1, wherein the longitudinal hollow-tubular-element-accepting channel has a smallest inner diameter of between 1.67 mm and 3 cm.

5. The apparatus according to claim 1, wherein the finger shield is configured to assume:
a shielding state, in which (a) a distal end of the finger shield is disposed more distally than the distal end of the radially-inner structure, and (b) a portion of the finger shield surrounds at least a longitudinal part of the protruding distal segment of the blade, and
a non-shielding state, in which (a) the distal end of the finger shield is disposed more proximally than when in the shielding state, and (b) the finger shield surrounds longitudinally less of the protruding distal segment of the blade than when in the shielding state.

6. The apparatus according to claim 5, wherein the finger shield is configured such that when the finger shield is in the shielding state, the portion of the finger shield completely radially surrounds the at least a longitudinal part of the protruding distal segment of the blade.

7. The apparatus according to claim 1,
wherein the pivot (a) extends radially out of the radially-inner structure and into a wall of the finger shield, and (b) is distally and proximally slidable within the wall of the finger shield, and
wherein the finger-shield spring, when loaded, is arranged to push the finger shield distally with respect to the radially-inner structure via the pivot.

8. The apparatus according to claim 1, wherein the tissue cutter further comprises a user control button, which is configured, upon depression of thereof, to advance the radially-inner structure distally with respect to the finger shield.

9. The apparatus according to claim 8, wherein the user control button is shaped so as to define a surface that is accessible from a proximal end of the housing.

10. The apparatus according to claim 1, wherein the blade is sterile.

11. The apparatus according to claim 1, wherein the tissue cutter is sterile.

12. The apparatus according to claim 1, wherein the tissue cutter comprises exactly one blade, exactly one pivot, and exactly one blade spring.

13. An apparatus comprising a kit, which comprises (a) a hollow tubular element having a tapered distal portion, and (b) a tissue cutter, which comprises:
a housing, which is shaped so as to define a longitudinal hollow-tubular-element-accepting channel that is shaped for slidable disposition therein of the hollow tubular element, and has proximal and distal openings and a central longitudinal axis;
a blade, which extends alongside the central longitudinal axis, and defines a sharp cutting surface that reaches a distal-most point of the blade and faces away from the central longitudinal axis;
a pivot, which couples the blade to the housing such that the blade is rotatable with respect to the housing around a pivot point of the blade; and
a blade spring, which is arranged to apply a force to the blade that pushes a distal portion of the blade against the tapered distal portion of the hollow tubular element when the blade is positioned alongside the tapered distal portion.

14. The apparatus according to claim 13, wherein the housing comprises:
- a radially-inner structure, which is shaped so as to define the longitudinal hollow-tubular-element-accepting channel, wherein the pivot couples the blade to the radially-inner structure, and wherein a protruding distal segment of the blade protrudes distally beyond a distal end of the radially-inner structure; and
- an outer finger shield, which is shaped so as to define a longitudinal radially-inner-structure-accepting channel that is shaped for slidable disposition therein of the radially-inner structure.

15. The apparatus according to claim 13, wherein the kit further comprises a guidewire, and wherein the hollow tubular element is shaped so as to define a longitudinal guidewire-accepting channel therethrough that is sized to accept the guidewire.

16. A method comprising:
- providing (a) a guidewire, (b) a hollow tubular element having a tapered distal portion, and shaped so as to define a longitudinal guidewire-accepting channel, and (c) a tissue cutter, which comprises:
  - a housing, which is shaped so as to define a longitudinal hollow-tubular-element-accepting channel that is shaped for slidable disposition therein of the hollow tubular element, and has proximal and distal openings and a central longitudinal axis;
  - a blade, which extends alongside the central longitudinal axis, and defines a sharp cutting surface that reaches a distal-most point of the blade and faces away from the central longitudinal axis;
  - a pivot, which couples the blade to the housing such that the blade is rotatable with respect to the housing around a pivot point of the blade; and
  - a blade spring, which is arranged to apply a force to the blade that pushes a distal portion of the blade against the tapered distal portion of the hollow tubular element when the blade is positioned alongside the tapered distal portion;
- placing a distal portion of the guidewire through an entry site on an external surface of skin of a subject and into an anatomic site, such that a proximal portion of the guidewire remains outside the skin;
- guiding the hollow tubular element and the tissue cutter over the proximal portion of the guidewire, until the tapered distal portion of the hollow tubular element and a distal end of the housing contact the external surface of the skin, while (a) the hollow tubular element is disposed in the longitudinal hollow-tubular-element-accepting channel with the blade positioned alongside the tapered distal portion, (b) the blade spring applies the force to the blade that pushes the distal portion of the blade against the tapered distal portion of the hollow tubular element, and (c) the guidewire is disposed in the longitudinal guidewire-accepting channel;
- thereafter, making an incision in the skin at the entry site by distally advancing the blade into the skin; and
- thereafter, advancing the hollow tubular element through the incision,
- wherein the housing comprises:
  - a radially-inner structure, which is shaped so as to define the longitudinal hollow-tubular-element-accepting channel, wherein the pivot couples the blade to the radially-inner structure, and wherein a protruding distal segment of the blade protrudes distally beyond a distal end of the radially-inner structure; and
  - an outer finger shield, which is shaped so as to define a longitudinal radially-inner-structure-accepting channel that is shaped for slidable disposition therein of the radially-inner structure, and
- wherein the tissue cutter further comprises a finger-shield spring, which is arranged to push the finger shield distally with respect to the radially-inner structure.

17. The method according to claim 16, wherein making the incision comprises distally advancing the blade into the skin while holding the hollow tubular element axially stationary.

18. The method according to claim 16, further comprising proximally withdrawing the tissue cutter after making the incision and before advancing the hollow tubular element through the incision.

19. The method according to claim 16,
- wherein the blade is a first blade, the sharp cutting surface is a first sharp cutting surface, the distal-most point of the blade is a first distal-most point of the blade, the pivot is a first pivot, the pivot point is a first pivot point, the blade spring is a first blade spring, the force is a first force, and the distal portion of the blade is a first distal portion of the blade, and
- wherein the tissue cutter further comprises:
  - a second blade, which extends alongside the central longitudinal axis, and defines a second sharp cutting surface that reaches a second distal-most point of the second blade and faces away from the central longitudinal axis in a second radial direction different from a first radial direction in which the first sharp cutting surface faces;
  - a second pivot, which couples the second blade to the housing such that the second blade is rotatable with respect to the housing around a second pivot point of the second blade; and
  - a second blade spring, which is arranged to apply a second force to the second blade that pushes a second distal portion of the second blade against the tapered distal portion of the hollow tubular element when the second blade is positioned alongside the tapered distal portion, and
- wherein the first and the second pivots couple the first and the second blades, respectively, to the radially-inner structure,
- wherein protruding distal segments of the first and the second blades, respectively, protrude distally beyond the distal end of the radially-inner structure, and
- wherein making the incision comprises making the incision in the skin by distally advancing the first and the second blades into the skin.

20. The method according to claim 19, wherein the first and the second blades rotate around the first and the second pivot points, respectively, by respective angles of between 1 and 45 degrees during a transition between (a) a first state in which the hollow tubular element holds the first and the second blades a distance apart and (b) a second state in which the hollow tubular element is not positioned alongside the first and the second blades, the distance equal to 95% of an inner diameter of the longitudinal hollow-tubular-element-accepting channel.

21. The method according to claim 16, wherein the longitudinal hollow-tubular-element-accepting channel has a smallest inner diameter of between 1.67 mm and 3 cm.

22. The method according to claim 16,
- wherein guiding comprises guiding the hollow tubular element and the tissue cutter over the proximal portion of the guidewire while the finger shield is in a shielding state, in which (a) a distal end of the finger shield is disposed more distally than the distal end of the radially-inner structure, and (b) a portion of the finger shield surrounds at least a longitudinal part of the protruding distal segment of the blade, and wherein making the incision comprises transitioning the finger shield to a non-shielding state, in which (a) the distal end of the finger shield is disposed more proximally than when in the shielding state, and (b) the finger shield surrounds longitudinally less of the protruding distal segment of the blade than when in the shielding state.

23. The method according to claim 22, wherein the finger shield is configured such that when the finger shield is in the shielding state, the portion of the finger shield completely radially surrounds the at least a longitudinal part of the protruding distal segment of the blade.

24. The method according to claim 16,
wherein the pivot (a) extends radially out of the radially-inner structure and into a wall of the finger shield, and (b) is distally and proximally slidable within the wall of the finger shield, and
wherein the finger-shield spring, when loaded, is arranged to push the finger shield distally with respect to the radially-inner structure via the pivot.

25. The method according to claim 16,
wherein the tissue cutter further comprises a user control button, which is configured, upon depression of thereof, to advance the radially-inner structure distally with respect to the finger shield, and
wherein making the incision comprises depressing the user control button.

26. The method according to claim 25,
wherein the user control button is shaped so as to define a surface that is accessible from a proximal end of the housing, and
wherein making the incision comprises depressing the surface of the user control button that is accessible from the proximal end of the housing.

27. The method according to claim 16, wherein the tissue cutter comprises exactly one blade, exactly one pivot, and exactly one blade spring.

28. A method comprising:
providing (a) a guidewire and (b) a kit, which comprises (i) a hollow tubular element having a tapered distal portion, and shaped so as to define a longitudinal guidewire-accepting channel therethrough that is sized to accept the guidewire, and (ii) a tissue cutter, which comprises:
a housing, which is shaped so as to define a longitudinal hollow-tubular-element-accepting channel that is shaped for slidable disposition therein of the hollow tubular element, and has proximal and distal openings and a central longitudinal axis;
a blade, which extends alongside the central longitudinal axis, and defines a sharp cutting surface that reaches a distal-most point of the blade and faces away from the central longitudinal axis;
a pivot, which couples the blade to the housing such that the blade is rotatable with respect to the housing around a pivot point of the blade; and
a blade spring, which is arranged to apply a force to the blade that pushes a distal portion of the blade against the tapered distal portion of the hollow tubular element when the blade is positioned alongside the tapered distal portion;
placing a distal portion of a guidewire through an entry site on an external surface of skin of a subject and into an anatomic site, such that a proximal portion of the guidewire remains outside the skin;
guiding the hollow tubular element and the tissue cutter over the proximal portion of the guidewire, until the tapered distal portion of the hollow tubular element and a distal end of the housing contact the external surface of the skin, while (a) the hollow tubular element is disposed in the longitudinal hollow-tubular-element-accepting channel with the blade positioned alongside the tapered distal portion, (b) the blade spring applies the force to the blade that pushes the distal portion of the blade against the tapered distal portion of the hollow tubular element, and (c) the guidewire is disposed in the longitudinal guidewire-accepting channel;
thereafter, making an incision in the skin at the entry site by distally advancing the blade into the skin; and
thereafter, advancing the hollow tubular element through the incision.

29. The method according to claim 28, wherein the housing comprises:
a radially-inner structure, which is shaped so as to define the longitudinal hollow-tubular-element-accepting channel, wherein the pivot couples the blade to the radially-inner structure, and wherein a protruding distal segment of the blade protrudes distally beyond a distal end of the radially-inner structure; and
an outer finger shield, which is shaped so as to define a longitudinal radially-inner-structure-accepting channel that is shaped for slidable disposition therein of the radially-inner structure.

30. The method according to claim 28, wherein the kit further comprises the guidewire.

* * * * *